United States Patent
Dabi et al.

(10) Patent No.: US 6,365,794 B1
(45) Date of Patent: Apr. 2, 2002

(54) MICROPOROUS FILMS COMPRISING FLOCKED FIBERS

(75) Inventors: Shmuel Dabi, Highland Park; Vincent P. Lasko, New Egypt, both of NJ (US); Rita S. Pilate, Washington Crossing, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/532,239

(22) Filed: Mar. 22, 2000

(51) Int. Cl.⁷ .............................................. A61F 13/20
(52) U.S. Cl. ...................... 604/367; 604/364; 604/365; 604/387; 604/378; 604/354
(58) Field of Search ............................. 604/354, 385.03, 604/385.23, 385.01, 384, 364, 367, 365, 387, 378

(56) References Cited

U.S. PATENT DOCUMENTS

| | | | |
|---|---|---|---|
| 3,779,246 A | * 12/1973 | Mesek et al. | 128/287 |
| 3,967,623 A | * 7/1976 | Butterworth et al. | 128/287 |
| 4,308,303 A | * 12/1981 | Mastroianni et al. | 428/90 |
| 4,324,246 A | 4/1982 | Mullane et al. | |
| 4,828,556 A | * 5/1989 | Braun et al. | 604/365 |
| 4,923,650 A | 5/1990 | Antoon, Jr. et al. | |
| 5,126,391 A | 6/1992 | Yamamato et al. | |
| 5,505,958 A | * 4/1996 | Bello et al. | 424/449 |
| 5,643,237 A | 7/1997 | Fechillas et al. | |
| 5,769,833 A | * 6/1998 | Hasse | 604/359 |
| 5,932,497 A | 8/1999 | Morman et al. | |
| 5,951,534 A | * 9/1999 | Cummings et al. | 604/359 |
| 6,028,017 A | * 2/2000 | Curtin et al. | 442/370 |

FOREIGN PATENT DOCUMENTS

| | | |
|---|---|---|
| EP | 0 737 462 A1 | 10/1996 |
| EP | 0 861 646 | 9/1998 |
| GB | 1 196 071 | 6/1970 |
| GB | 2 077 142 | 12/1981 |

OTHER PUBLICATIONS

European Search Report (Application No. EP 00 11 5481).

* cited by examiner

Primary Examiner—John G. Weiss
Assistant Examiner—Michael Bogart

(57) ABSTRACT

This invention relates to microporous films comprising flocked fibers. Such microporous films may be used as breathable materials in for example absorbent articles, wound care bandages, and skin care patches.

18 Claims, 1 Drawing Sheet

MICROPOROUS FILMS COMPRISING FLOCKED FIBERS

The present invention relates to microporous films comprising flocked fibers, which provide a desirable, breathable material that may be used for example in absorbent articles, wound care products, and skin care products.

BACKGROUND OF THE INVENTION

"Breathable" materials are those that allow gases but not liquids to pass through them. They have found advantageous application as breathable backsheets for products like absorbent articles, such as sanitary napkins and pantiliners. They are also employed in wound care products such as bandages that provide protection from dirt, germs, and water while maintaining an ideal environment for would healing.

Common breathable materials include polyurethane films, microporous films, and laminates of permeable films and nonwovens. Conventional microporous films are made by subjecting a film to ionizing radiation or by leaching out of soluble inclusions on the film using aqueous or nonaqueous solvents. Alternatively, microporous films are made by incorporating micron size particles into an extruded film, followed by controlled stretching of the film to create small voids in it. See for example, U.S. Pat. Nos. 4,923,650 and 5,126,391. However, microporous films by themselves are generally not soft feeling and do not mimic the texture of fabric very well. On the other hand, they have excellent resistance to strike through by liquids.

A variety of film/nonwoven laminates are also known to provide breathability. Such laminates advantageously have the attributes of a fabric. For example, U.S. Pat. No. 5,932,497 discloses a breathable film loaded with a filler and stretched in at least two directions laminated to a nonwoven web.

Flocking is a technique by which fibers are fixed in a vertical position on a substrate, and is primarily used in the fabric industry. However, EP 0 737 462 A1 discloses a laminated material to cover the outside of an absorbent product such as a sanitary napkin, characterized in that at least one portion of the surface of the laminated material bears a layer of fibers applied by flocking. The flocked fibers are thereby located on the external surface of the absorbent product in order to give the absorbent product improved tactile properties over products that employ plastic films against the skin.

It has now been discovered that a microporous film comprising flocked fibers may be made. Such a composite material provides good breathability with low liquid strike through. It may be used in absorbent articles, in particular as a backsheet on sanitary protection articles. It may also be used as a component of a wound care bandage or skin care patch. Surprisingly, the application of flocked fibers to a microporous film does not impair its overall breathability. At the same time, the microporous film is endowed with a soft surface. The flocking also provides a vehicle for holding additives like moisturizers, medicaments, and the like on the microporous film.

SUMMARY OF THE INVENTION

The invention provides a microporous film comprising flocked fibers, as well as an absorbent article, wound care bandage, or skin care patch comprising such a microporous film.

DETAILED DESCRIPTION OF THE INVENTION

Figure 1:
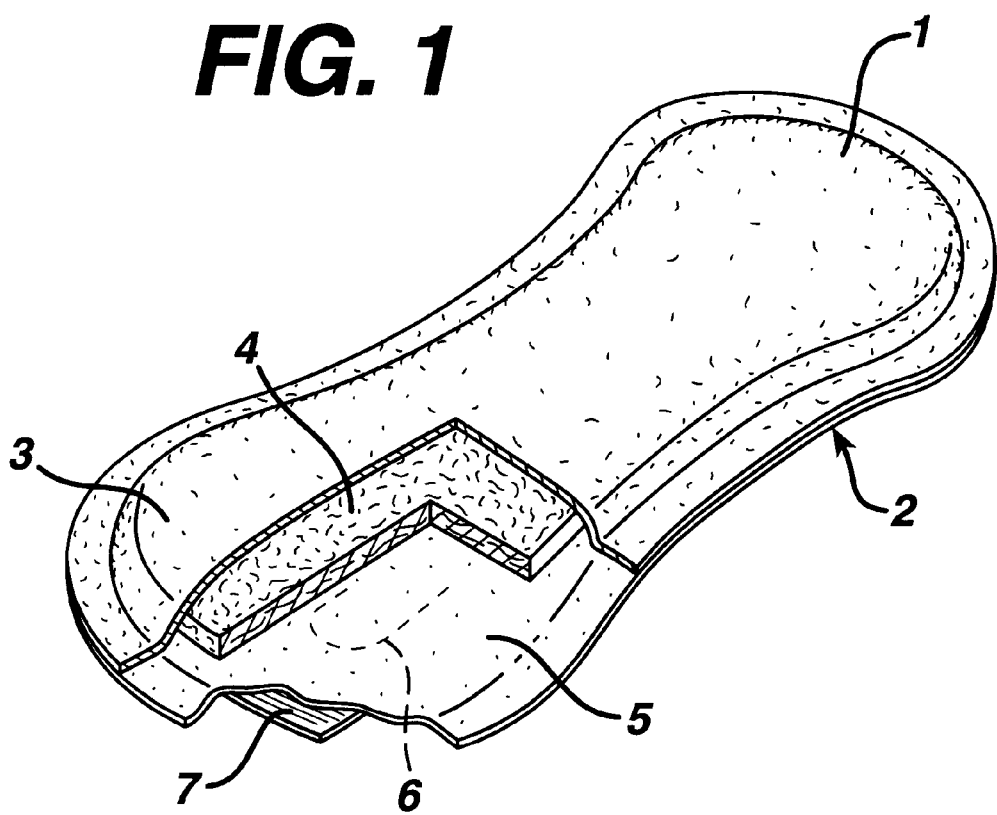
FIG. 1 depicts a pantiliner comprising a backsheet made from a microporous film comprising flocked fibers.

The microporous film may be of any type. The nature of the microporous film is not critical to the invention. Examples of microporous films include the EXAIRE XBF series of microporous films commercially available from Tredegar Industries, Inc. and 3M Microporous Film and 3M Face Fresh'ner Film both commercially available from 3M.

The flocked fibers may be hydrophilic, hydrophobic, or a combination of the two. Hydrophilic fibers include wettable fibers, i.e., hydrophobic fibers that have been treated with a wetting agent to render them hydrophilic, absorbent fibers, and superabsorbent polymer fibers. Examples of wettable fibers include bicomponent fibers, polypropylene fibers, and polyester fibers that have been treated for example with surfactants. Preferred wettable fibers are polyester fibers, such as DuPont-Akra Polyester Type 11A Bright commercially available from DuPont Company treated with a surfactant such as Tween 20 commercially available from ICI Americas Inc.

Absorbent fibers are hydrophilic fibers that both that have an affinity for and absorb fluids. Absorbent fibers may comprise rayon fibers, acrylic fibers, nylon fibers, polyvinyl alcohol fibers, and fibers of natural or regenerated cellulosics. A preferred type of absorbent fiber is rayon fibers.

Superabsorbent polymer fibers are hydrophilic fibers that are swellable and capable of absorbing greater than about 5 grams per gram (of fiber weight) of 1% saline solution. Examples of superabsorbent polymer fibers are polyacrylate fibers, fibers of grafted cellulose, and fibers of maleic acid. Preferred types of superabsorbent polymer fibers include OASIS Type 101, commercially available from Technical Absorbents Limited and CAMELOT, commercially available from Camelot, Alberta, Canada.

Hydrophobic fibers include certain olefin fibers and large denier polyester fibers, preferably having a denier of at least 3, more preferably at least 6. A preferred hydrophobic fiber is 15 denier polyester commercially available from DuPont Company.

Regardless of type, the length of the flocked fibers should be less than about 1 mm, preferably less than about 0.8 mm. The denier of the flocked fibers should be in the range of about 1.2d to about 15d, preferably about 1.8d to about 6d.

In a particularly preferred embodiment of the invention, the flocked fibers comprise cotton or rayon, preferably having a denier of 3 or less. A microporous film bearing such fibers is particularly suitable for use in absorbent articles, especially sanitary protection articles, for example as a breathable backsheet.

The fibers are applied to one or more surfaces of the microporous film by the process of flocking. Methods of flocking fibers onto a surface are known in the art of fabric manufacture. See for example, U.S. Pat. Nos. 2,527,501; 2,691,611; 3,436,442; and 3,672,929. Typically, the microporous film is coated with adhesive on all or a portion of its surface. The coated microporous film is then passed through a fiber metering station, in which an electrostatic field is maintained around it, using for example electrodes situated above and below the microporous film. The fibers are applied to the adhesive on the microporous film in the presence of the electrostatic field, which orients the fibers perpendicular to the microporous film as they contact the adhesive. The microporous film is then heated, polymerizing the adhesive and anchoring the fibers. Care should be taken not to crosslink or cure the adhesive. Unattached fibers may be vacuumed away.

Preferably, the adhesive employed to attach the fibers to the microporous film is a polymerizable resin, such as modified acrylic water based compounds, for example FLEXBOND 974, 977, 983, and 986 commercially available from Air Products, CARBOTAC Adhesives (PSAs) commercially available from B F Goodrich, and CARBOBOND Adhesives (non-PSAs) also commercially available from B F Goodrich.

The flocked fibers may be adhered to all or a portion of the microporous film. The flocked fibers may be on one or both sides of the microporous film. The same or different flocked fibers may be on two or more different areas or sides of the microporous film. Mixtures of different types of flocked fibers may also be employed. Depending on the intended use of the microporous film, the nature and amount of flocked fibers thereon can be tailored accordingly.

The microporous film may comprise one or more additives such as odor control agents, perfumes, medicaments, moisturizing compositions, and the like, many examples of which are known in the art. The additive may be dispersed within the flocked fibers, which act as a vehicle for holding the additive.

The microporous film comprising flocked fibers is particularly useful as a breathable backsheet for an absorbent article. The absorbent article may for example be a sanitary protection product, such as a sanitary napkin, pantiliner, diaper, incontinence pad, interlabial article, or other similar product for absorbing exudates from the body, such as menses, urine, or feces. Such sanitary napkin or pantiliner may have an approximately rectangular, oval, dogbone, or peanut shape. Depending on the nature of the absorbent article, its size may vary. For example, sanitary napkins typically have a caliper of about 1.4 to about 5 mm, a length of about 3 to about 16 inches, and a width of about 1 to about 5 inches. Pantiliners typically have a caliper of less than about 0.2 inches, a length of less than about 8 inches, and a width of less than about 3 inches.

FIG. 1 depicts a pantiliner comprising a backsheet made from a microporous film comprising flocked fibers, and is used for purposes of illustration in the following description. The pantiliner shown in FIG. 1 comprises in sequence from its body-facing surface 1 to its garment-facing surface 2 liquid permeable cover 3, an absorbent core 4, and a backsheet 5 comprising the microporous film. The cover 3 of the absorbent article may be formed from any fluid pervious material that is comfortable against the skin and permits fluid to penetrate to the absorbent core, which retains the fluid. The cover should retain little or no fluid to provide a relatively dry surface, since its external surface forms the body-facing surface 1 of the article. A variety of materials are known for preparing covers, and any of these may be used. For instance, the cover may be a fibrous non-woven fabric made of natural or polymeric fibers or filaments such as polyethylene, polypropylene, polyester, or cellulose. Alternatively, the cover may be formed from an apertured polymeric film. The thickness of the cover may vary from approximately 0.001 to 0.062 inch, depending on the material chosen.

Generally, cover 3 is a single sheet of material having a width sufficient to form the body-facing surface 1 of the article. The cover may be the same length, or optionally longer than the absorbent core so as to form transverse ends. Such transverse ends may be sealed with other layers to fully enclose the absorbent core.

The absorbent core 4 may be comprised of a loosely associated absorbent hydrophilic material such as cellulose fibers, including wood pulp, regenerated cellulose fibers or cotton fibers, or other absorbent materials generally known in the art, including acrylic fibers, polyvinyl alcohol fibers, peat moss and superabsorbent polymers.

The exterior of backsheet 5 forms the garment-facing surface 2 of the article. When the microporous film comprising flocked fibers is used as a breathable backsheet, the flocked fibers are preferably present on the surface of the microporous film that forms the garment-facing surface 2 of the article.

Generally, the width of the backsheet 5 is sufficient to form the garment-facing surface 2 of the absorbent article. The backsheet may extend around the sides of the absorbent core in a C-shaped configuration with the portions of the backsheet adjacent its longitudinal edges extending upwardly from the garment-facing surface toward the body-facing surface of the article.

The absorbent article may be applied to the crotch of underpants by placing the garment-facing surface 2 of the absorbent article against the inside surface of the crotch of the underpants. Strips of pressure sensitive adhesive 6 may be applied to the garment-facing surface 2 of the absorbent article to help maintain it in place. As used herein, the term "pressure-sensitive adhesive" refers to any releasable adhesive or releasable tenacious means. Suitable pressure sensitive adhesives include for example water-based adhesives such as acrylate adhesives. Alternatively, the adhesive may comprise rapid setting thermoplastic "hot melt" rubber adhesives or two-sided adhesive tape.

A paper release strip 7 that has been coated on one side may be applied to protect the strips of adhesive 6 prior to use. The coating, for example silicone, reduces adherence of the coated side of the release strip to the adhesive. The release strip can be formed from any suitable sheet-like material which, when coated, adheres with sufficient tenacity to the adhesive to remain in place prior to use but can be readily removed when the absorbent article is to be used.

The absorbent article may comprise other known materials, layers, and additives, such as transfer layers, foam layers, net-like layers, and the like. The absorbent article can optionally be embossed with decorative designs using conventional techniques.

The microporous film comprising flocked fibers may also be used, for example, as a component of a wound care bandage. In such a wound care bandage, the microporous film may be used as a backing material, which can for example be coated with a pressure sensitive adhesive and attached to an absorbent pad. The flocked fibers can be either on the outer surface of the bandage, providing low friction and low self adhesion for removal and aesthetics, or on the inside surface of the bandage, facing the skin for softness and absorbency. The wound care bandage may further comprise other optional components known in the art.

The microporous film comprising flocked fibers may also be used as a skin care patch, preferably disposable, for delivering moisturizing compositions, medicaments, perfumes, odor control agents, and the like to the skin. For example, a skin care patch may comprise a microporous film with flocked fibers on one side. Dispersed within the flocked fibers is a moisturizing composition, for example comprising glycerin.

In another embodiment of the invention, such a skin care patch may comprise one or more medicaments or natural ingredients dispersed within the flocked fibers. Examples of medicaments include salicylic acid, retinol, and benzoyl peroxide. Examples of natural ingredients include soy milk, menthol, and vitamins A, C and E. Adhesive may be applied over the medicament-containing flocked fibers, preferably in a discontinuous pattern, so that the skin care patch may be temporarily attached to the skin.

The following example further illustrates the invention, but us not intended to limit the claimed invention.

EXAMPLE 1

A microporous film according to the invention comprising flocked fibers of cotton is made as follows. EXAIRE TDO-XBF-116W, a 35 gsm microporous film commercially available from Tredegar is employed. A polymerizable resin is applied to the microporous film by rotary screen printing. Cotton fibers having a denier of less than 3 are metered onto the microporous film. The fibers are oriented in the vertical position via an electrostatic field. The fibers adhere where the resin has been applied. The film is then passed through an oven to polymerize the resin, anchoring the fibers to the film. The excess fibers are vacuumed away.

The microporous film may be used a breathable backsheet in a pantiliner.

EXAMPLE 2

A non-occlusive skin care patch for the delivery of an acne-treating medicament is made according to the invention as follows. 3M Microporous Film is coated with flocked fibers in the same manner as Example 1 to form a 5 mil layer of flocking on one surface. A water solution containing 20% by weight of polyvinyl pyrrolidone (Kollidon 90 commercially available from BASF), 3% glycerin and 2% salicylic acid is applied to the fiber-bearing side of the film and irradiated with a 2.5 Mrad energy electron beam to crosslink the polyvinyl pyrrolidone and form a stable, sticky gel. The final laminate is cut into various sizes for applying to skin for acne treatment.

EXAMPLE 3

A disposable wound care bandage according to the invention is made as follows. 3M Microporous Film is coated with hydrophobic flocked fibers comprising polypropylene and polyester on one side in the manner described in Example 1. The non-flocked side of the film is spray coated with HL 1417, a pressure sensitive, hot melt adhesive commercially available from H. B. Fuller. An absorbent pad is made by laminating a needle punched 90/10 polypropylene/rayon fabric having a basis weight of 60 gsm with a Delnet apertured film, commercially available from the AET company.

A 70×20 mm strip of the flocked, microporous film is cut. A 20×20 mm square of the absorbent pad is cut and glued via its fabric side to the adhesive side of the flocked film to form the wound are bandage.

We claim:

1. A microporous film comprising flocked superabsorbent polymer fibers.

2. The microporous film of claim 1, further comprising flocked fibers selected from the group consisting of hydrophilic fibers, hydrophobic fibers and mixtures thereof.

3. The microporous film of claim 2, wherein the hydrophilic fibers are selected from the group consisting of wettable fibers, absorbent fibers and mixtures thereof.

4. The microporous film of claim 2, wherein the flocked fibers are selected from the group consisting of cotton, rayon, and mixtures thereof.

5. The microporous film of claim 1 further comprising an additive selected from the group consisting of moisturizing compositions, medicaments, perfumes, odor control agents, and mixtures thereof.

6. The absorbent article comprising a microporous film, wherein the microporous film comprises flocked superabsorbent polymer fibers.

7. The absorbent article of claim 6, wherein the microporous film is a backsheet for the absorbent article.

8. The absorbent article of claim 6, wherein the microporous film further comprises flocked fibers selected from the group consisting of hydrophilic fibers, hydrophobic fibers and mixtures thereof.

9. The absorbent article of claim 8, wherein the hydrophilic fibers are selected from the group consisting of wettable fibers, absorbent fibers, and mixtures thereof.

10. The absorbent article of claim 8, wherein the flocked fibers are selected from the group consisting of cotton, rayon, and mixtures thereof.

11. A sanitary napkin comprising a microporous film, wherein the microporous film comprises flocked superabsorbent polymer fibers.

12. A pantiliner comprising a microporous film, wherein the microporous film comprises flocked superabsorbent polymer fibers.

13. A wound care bandage comprising a microporous film, wherein the microporous film comprises flocked superabsorbent polymer fibers.

14. A skin care patch comprising a microporous film, wherein the microporous film comprises flocked superabsorbent polymer fibers.

15. The skin care patch of claim 14 further comprising a moisturizing composition dispersed within the flocked fibers.

16. The skin care patch of claim 15, wherein the moisturizing composition comprises glycerin.

17. The skin care patch of claim 14 further comprising a medicament dispersed within the flocked fibers.

18. The skin care patch of claim 17 wherein the medicament comprises salicylic acid.

* * * * *